(12) United States Patent
Dal Farra et al.

(10) Patent No.: US 9,259,381 B2
(45) Date of Patent: Feb. 16, 2016

(54) USE OF A CORN PEPTIDIC HYDROLYZATE AS AN ACTIVE AGENT STIIMULATING HAIR GROWTH

(71) Applicants: Claude Dal Farra, Kerhonkson, NY (US); Nouha Domloge, Valbonne (FR); Jean-Marie Botto, Valbonne (FR)

(72) Inventors: Claude Dal Farra, Kerhonkson, NY (US); Nouha Domloge, Valbonne (FR); Jean-Marie Botto, Valbonne (FR)

(73) Assignee: ISP INVESTMENTS INC., Wilmington, DE (US)

( * ) Notice: Subject to any disclaimer, the term of this patent is extended or adjusted under 35 U.S.C. 154(b) by 408 days.

(21) Appl. No.: 13/858,262

(22) Filed: Apr. 8, 2013

(65) Prior Publication Data

US 2013/0225504 A1 Aug. 29, 2013

Related U.S. Application Data

(63) Continuation of application No. 13/505,509, filed as application No. PCT/FR2010/000723 on Nov. 2, 2010, now abandoned.

(30) Foreign Application Priority Data

Nov. 3, 2009 (FR) ..................................... 09 05258

(51) Int. Cl.
| | | |
|---|---|---|
| *A61K 36/00* | (2006.01) | |
| *A61K 36/899* | (2006.01) | |
| *A61K 8/64* | (2006.01) | |
| *A61K 8/97* | (2006.01) | |
| *A61Q 5/00* | (2006.01) | |
| *A61Q 7/00* | (2006.01) | |

(52) U.S. Cl.
CPC . *A61K 8/645* (2013.01); *A61K 8/97* (2013.01); *A61K 36/899* (2013.01); *A61Q 5/00* (2013.01); *A61Q 7/00* (2013.01)

(58) Field of Classification Search
None
See application file for complete search history.

(56) References Cited

U.S. PATENT DOCUMENTS

| | | | |
|---|---|---|---|
| 4,139,619 A | | 2/1979 | Chidsey, III |
| 4,596,812 A | | 6/1986 | Chidsey, III |
| 7,431,919 B2 | * | 10/2008 | Travkina et al. ............. 424/70.7 |
| 7,468,265 B2 | | 12/2008 | Ishimaru et al. |
| 8,080,524 B2 | | 12/2011 | Bakala et al. |
| 2005/0089934 A1 | | 4/2005 | Ishimaru et al. |

FOREIGN PATENT DOCUMENTS

| | | | |
|---|---|---|---|
| AU | B-6724394 | * | 12/1994 |
| CH | 682217 | | 8/1993 |
| DE | 3130894 | | 2/1983 |
| EP | 1885323 | | 2/2008 |
| FR | 2904543 | | 2/2008 |
| FR | 2911070 | | 7/2008 |
| FR | 2915382 | | 10/2008 |
| FR | 2925326 | | 6/2009 |
| GB | 2060378 | | 5/1981 |
| JP | 01-128912 | | 5/1989 |
| JP | 02-078608 | | 3/1990 |
| JP | 07-285880 | | 10/1995 |
| JP | 07-316023 | | 12/1995 |
| JP | 2005239624 A | * | 9/2005 |
| WO | 2010/119192 | | 10/2010 |

OTHER PUBLICATIONS

Birch, M.P. et al., "Hair density, hair diameter and the prevalence of female pattern hair loss," *British Journal of Dermatology*, 144, pp. 297-304 (2001).
Botchkarev, V.A. et al., "p53 Involvement in the Control of Murine Hair Follicle Regression," *American Journal of Pathology*, vol. 158, No. 6, pp. 1913-1919 (Jun. 2001) .
Chikh, A. et al., "Expression of GATA-3 in epidermis and hair follicle: Relationship to p63 " *Biochemical and Biophysical Research Communications*, 361, pp. 1-6 (2007).
Commo, S. et al., "The distribution of a2β1, a3β1 and a6β4 integrins identifies distinct subpopulations of basal keratinocytes in the outer root sheath of the human anagen hair follicle," *CMLS Cellular and Molecular Life Science*, 53, pp. 466-471 (1997).
Courtois, M. et al., "Ageing and hair cycles," *British Journal of Dermatology*, 132, pp. 86-93 (1995).
Etukudo, M. et al., "Biochemical changes and liver tissue pathology in weanling Wistar albino rates with protein energy malnutrition (PEM)," *Discover and Innovation*, vol. 11, No. 1-2, pp. 83-89 (Mar. 1959).
Foitzik, K. et al., "Control of murine hair follicle regression (catagen) by TGF-β1 in vivo," *The FASEB Journal*, vol. 14., pp. 752-760 (Apr. 2000).
Langbein, L. et al., "The Catalog of Human Hair Keratins," *The Journal of Biological Chemistry*, vol. 276, No. 37, pp. 35123-35132 (Sep. 2001).
Lenoir, M-C. et al., "Outer Root Sheath Cells of Human Hair Follicle Are Able to Generate a Fully Differentiated Epidermis in Vitro," *Development Biology*, 130, pp. 610-620 (1988).
Mouser, P. et al., "Modulation of hair growth markers in the hair follicle," 6th World Congress for Hair Research, Cairns, Australia (Jun. 2010).
Osborne, T.B., The Vegetable Proteins, Second Edition, published by Longmans, Green and Co., London, 1924, Chapters IX and X, pp. 68-154.
Porter, R.M. et al., "Keratin K6irs is specific to the inner root sheath of hair folicles in mice and humans," *British Journal of Dermatology*, 145, pp. 558-568 (2001).
Squibb, R.L. et al., "A Comparison of the Effect of Raw Corn and Tortillas (Lime-Treated Corn) with Niacin, Tryptophan or Beans on the Growth and Muscle Niacin of Rats," *The Journal of Nutrition*, vol. 67, No. 3, pp. 351-361 (1959).
PCT, International Search Report, International Application No. PCT/FR2010/000723 (mailed May 19, 2011, published Jun. 30, 2011).

*Primary Examiner* — Qiuwen Mi
(74) *Attorney, Agent, or Firm* — Thompson Hine LLP

(57) ABSTRACT

The invention relates to a cosmetic treatment method intended to stimulate hair growth, restore hair growth, and/or limit hair loss. The cosmetic treatment method includes providing a composition comprising at least one corn (*Zea mays* L.) peptidic hydrolyzate, as an active agent to stimulate hair growth, or reduce hair loss and applying it topically to an area having hair follicles.

15 Claims, 1 Drawing Sheet

(56) References Cited

OTHER PUBLICATIONS

PCT, International Preliminary Report on Patentability, International Application No. PCT/FR2010/000723 (Jun. 5, 2012).

Office Action, U.S. Appl. No. 13/505,509 (Jul. 26, 2012).
Office Action, U.S. Appl. No. 13/505,509 (Sep. 27, 2012).
Office Action, U.S. Appl. No. 13/505,509 (Jan. 9, 2013).

* cited by examiner

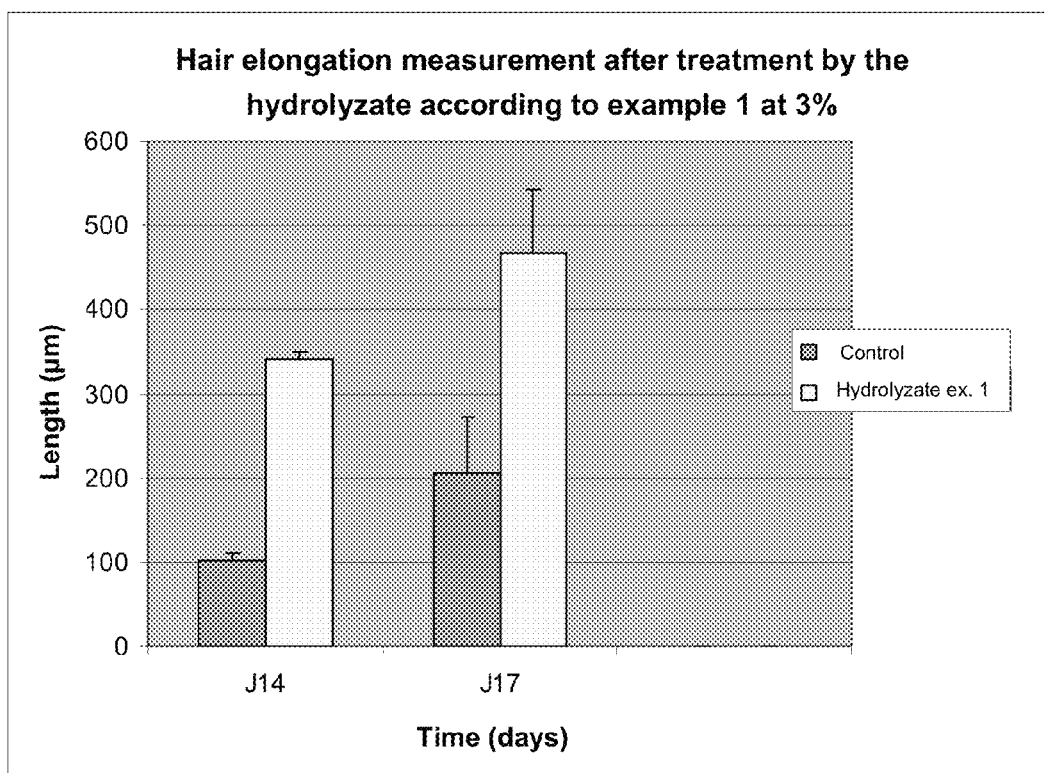

USE OF A CORN PEPTIDIC HYDROLYZATE AS AN ACTIVE AGENT STIIMULATING HAIR GROWTH

REFERENCE TO RELATED CASE

This application is a continuation of U.S. application Ser. No. 13/505,509, filed May 2, 2012, which was the National Stage of International Application No. PCT/FR2010/000723, filed Nov. 2, 2010, which claims benefit of French Application No. 0905258, filed Nov. 3, 2009.

FIELD OF THE INVENTION

The present invention is situated in the cosmetic and dermato-pharmaceutical field. The invention relates to the cosmetic use of a composition comprising at least one corn (*Zea mays* L.) peptidic hydrolyzate, as an active agent to stimulate and/or restore hair growth, or prevent hair loss. The active agent comes from the hydrolysis of plant proteins chosen from among plants of the *Zea* genus, and more specifically of the *Zea maïs* L. species. The invention is also relative to the use of this novel active agent to produce a dermato-pharmaceutical composition intended to stimulate and/or restore hair growth, or prevent hair loss, in the context of a preventive or curative treatment for hair loss connected to a pathological condition.

The invention further applies to a cosmetic treatment process intended to prevent or combat manifestations of hair aging, according to which a composition containing the active agent is applied topically to the areas to be treated.

BACKGROUND OF THE INVENTION

Hair growth and renewal are mainly determined by the activity of hair follicles and their matrix environment.

The hair follicle is a complex autonomous cutaneous annex that comprises six large compartments, some of dermic origin (connective tissue sheath and hair papilla), others of an epithelial nature (inner and outer root sheath, hair shaft and sebaceous gland). At the base of the follicle the matrix is found, which is the site of intense mitotic activity, at the origin of 3 concentric layers of hair essentially constituted of keratin.

The hair follicle renews in situ in a cyclic and asynchronous manner from a double reservoir of stem cells, according to an activity cycle that comprises three phases: The anagen phase, the catagen phase and the telogen phase.

The anagen phase (growth phase) lasts from one to ten years and is characterized by the constant elongation of the hair. During this phase, the outer root sheath cells overexpress beta 1 integrin (Commo & Bernard, 1997, Cell mol. life Sc. 53:466-471). The proliferative cells from this area express proliferation markers such as the Ki67 protein and the p63 transcription factor (Chikh et al., 2007, Biochem Biophys Res Commun., 14; 361(1):1-6).

The following catagen phase is very transient and lasts some weeks. It seems to be initiated by certain factors such as EGF, TGF beta (Foitzik et al. 2000, FASEB J. 14(5):752-60), or else the p53 protein that is temporarily overexpressed (Botchkarev et al., 2001, Am. J. Pathol. 158(6): 1913-1919). During this phase, the follicle cells undergo an active apoptosis process, the follicle atrophies and retracts to the surface, with the well-known exception of the hair papilla that will be the key element in future regeneration.

The terminal phase or telogen phase, which lasts some months, corresponds to a follicle rest phase at the end of which the hair finishes by falling. At the end of this rest period, a new follicle is regenerated and a new cycle starts.

In addition, it has been clearly described that the differentiation mechanisms of keratinocytes from the epidermis and hair follicle are substantially different. Therefore, it is known that keratins from the hair shaft represent a family of keratins that is distinct from that expressed in the epidermis (Langbein et al., 2001, J. Biol. Chem. 276), thus the K6irs keratin (Porter et al., 2001, Br. J. Dermatol. 145: 558-568) is expressed in the inner sheath of the hair follicle but not in the epidermis, while epidermal differentiation markers such as K1 and K10 keratins are not expressed in the hair follicle (Lenoir et al., 1988, Dev. Biol. 130: 610-620).

The natural fall or loss of hair may be estimated, on average, as a hundred hairs per day for a normal physiological condition. This ongoing renewal process may be disturbed by many extrinsic and intrinsic factors, leading to a significant loss of hair, temporary or definitive, that may be grouped together under the generic term of alopecia.

As with the rest of the organism, the ongoing physiological hair renewal process is subject to aging. Whereas the most visible sign of hair aging is the graying of hair, the quality of the biological environment of the hair follicle is also affected. From among the manifestations of hair aging are observed a lesser protein synthesis of the extracellular matrix (collagen, laminin, fibronectin), leading to a loss of elasticity and tonus of the subcutaneous tissue. There is also a reduction in the consistency and organization of hair follicles, a reduction in the anagen phase duration and an extension in the telogen phase duration (Courtois et al., 1995, Br. J. dermatol., 132: 86-93). In fact, the hair loses its elasticity, it is more fine and therefore more fragile. With regard to the entire scalp, aging is manifested by a lowering in capillary density and by the progressive reduction in follicle diameter, giving the hair a poorer, more sparse appearance (Pelfini, C. et al., J. Méd. Esth. Et Chir. Derm 1987; Birch M P et al. Br. J. Dermatol 2001; 144:297-304).

Independently from intrinsic aging, alterations in the hair or hair follicle may be produced during external stresses. In fact, whereas the hair has a remarkable stability, certain external factors, such as the sun, responsible for photoaging, free radicals, pollution or else certain inappropriate treatments may result in a premature deterioration in the hair structure and depletion of follicles.

The expression "external stress" is understood to refer to stresses that the environment may produce. By way of example, stresses such as pollution, UV radiation or else products with an irritating character such as surface active agents that are too detergent, colorings and bleachings, too frequent permanents or hair straightening treatments, mechanical stresses such as the rubbing of clothes, hair styles causing repeated stretching of the hair, too intense brushing, blow-dryings and drying with air that is too hot may be cited. Pollution is understood to refer to both "external" pollution, due for example to diesel particles, ozone or heavy metals and to "internal" pollution, that may be particularly due to the emissions from paint, adhesive or wallpaper solvents (such as toluene, styrene, xylene or benzaldehyde), or else to cigarette smoke. These external stresses result in an alteration in the external structure of the hair and in its mechanical properties, but may also affect the hair follicle and cause premature aging.

The cosmetic or pharmaceutical industry always seeks compositions eliminating or reducing hair loss or stimulating hair growth. As a known molecule, 2,4-diamino 6-piperidinopyrimidine 3-oxide or "minoxidil" (patents U.S. Pat. No. 4,139,619 and U.S. Pat. No. 4,596,812) may be cited. Another patent document by Shiseido (JP 07316023) also describes the use of arginine and its derivatives in the treatment of alopecia. Lastly, document EP 1885323 describes the use of a synthetic peptide to stimulate hair growth.

However, certain available products present side effects, such as in the case of minoxidil, or have a relative effectiveness confined to the treatment duration. Also, a need remains for a novel physiologically acceptable composition to encourage hair growth and/or reduce hair loss, presenting a rapid and long-lasting action.

Corn peptidic extracts have previously been described for their effects on the skin (FR 2904543, FR 2915382, FR 2925326).

The inventors have now demonstrated that such corn peptidic hydrolyzates have an activity on the hair follicle. In particular, it has been demonstrated that the peptidic hydrolyzate, when it is applied to the hair, activates the hair follicle and stimulates hair growth.

DISCLOSURE OF THE INVENTION

The first object of the present invention is the cosmetic use of a composition comprising at least one corn (*Zea mays* L.) peptidic hydrolyzate as an active agent to stimulate and/or restore hair growth, or prevent hair loss.

The human keratin fibers to which the invention applies are, in particular, hair, eyebrows, eyelashes, beard, mustache and pubic hair and nails. More especially, the invention applies to human hair and/or eyelashes.

"Peptidic hydrolyzate" is understood to refer to a mixture of compounds predominantly represented by peptides or oligopeptides. According to the invention, the terms "peptidic hydrolyzate" or "active agent" will be used equally.

"Active agent to stimulate and/or restore hair growth, or prevent hair loss" is understood to refer to any corn (*Zea mays* L.) peptidic hydrolyzate capable of stimulating the hair follicle, i.e., increase the expression of the main molecules of the extracellular matrix such as fibronectin, the basal lamina such as laminin-5 and the principal intracellular markers of the anagen phase of the hair follicle, such as beta 1 integrin, the Ki67, p63 proliferation markers and phosphorylated histone H3, or on the contrary, of inhibiting the expression of catagen phase initiators, such as the p53 protein, thus enabling an extension of the hair growth anagen phase.

The active agent according to the invention may be obtained by extraction of proteins of plant origin, followed by a controlled hydrolysis that releases the peptidic nature compounds.

"Peptidic nature compounds" is understood to refer to fragments of proteins and peptides present in the peptidic hydrolyzate according to the invention.

The utilization of peptidic hydrolyzates, particularly low molecular weight peptidic hydrolyzates, presents many advantages in cosmetics. In addition to generating peptidic nature compounds that did not preexist in the starting protein mixture, hydrolysis and purification enable more stable mixtures to be obtained, that are easy to standardize and that do not cause dermatological and cosmetic allergic reactions.

Very many plant proteins are likely to contain bioactive peptides within their structure. Controlled hydrolysis enables these peptidic nature compounds to be released. It is possible, but not necessary to carry out the invention, to extract either the relevant proteins first and then hydrolyze them, or perform hydrolysis first on a crude extract and then purify the peptidic nature compounds.

According to a preferred embodiment, said active agent comes from the hydrolysis of plant proteins chosen from among plants of the *Zea* genus and preferentially the *Zea mays* L. species. According to the invention, the plant material utilized will be the seed and, preferentially, the hull of the seed was removed by a hulling step. Preferably, the plants used are not subjected to prior fermentation.

Any extraction or purification method known to the person skilled in the art may be utilized in order to prepare the hydrolyzate according to the invention.

In a first step, the seeds are ground by using a plant mill. The powder thus obtained may subsequently be de-fatted by using a conventional organic solvent (such as for example an alcohol, hexane or acetone).

Then proteins are extracted according to the modified conventional method (Osborne, 1924); the plant ground material is suspended in an alkaline solution containing an adsorbent product of the insoluble polyvinylpolypyrrolidone (PVPP) type (0.01-20%); In fact, it was observed that subsequent hydrolysis and purification operations were facilitated by this means. In particular, the concentration of phenolic type substances, interacting with proteins, is markedly reduced.

The soluble fraction, containing proteins, carbohydrates and possibly lipids, is collected after the centrifugation and filtration steps. This crude solution is then hydrolyzed under controlled conditions to generate peptides. Hydrolysis is defined as being a chemical reaction involving cleavage of a molecule by water, this reaction may be done in neutral, acidic or basic medium. According to the invention, hydrolysis is carried out chemically and/or advantageously by proteolytic enzymes. The utilization of plant origin endoproteases (papain, bromelin, ficin) and microorganisms (*Aspergillus, Rhizopus, Bacillus*, Novozyme Alcalase®, etc.) may then be cited.

For the same reasons as above, i.e., the elimination of polyphenolic substances, a quantity of polyvinylpolypyrrolidone is added to the reaction medium during this controlled hydrolysis step. After the filtration step, enabling the enzymes and polymers to be eliminated, the filtrate (solution) obtained constitutes a first form of the active agent according to the invention.

The hydrolyzate obtained at this stage may again be purified in order to select the peptidic nature compounds with a molecular weight of less than 10 kDa. The fractionation may advantageously be carried out by successive ultrafiltration steps through filters of decreasing porosity by conserving the filtrates at each step. After this step, the majority of peptidic nature compounds contained in the hydrolyzate and preferentially 90% of them, have a molecular weight of less than 5 kDa.

The peptidic hydrolyzate obtained according to the invention is qualitatively and quantitatively analyzed for its physical chemical characteristics and its peptidic nature compound content. The protein peptides and fragments are measured according to conventional techniques, well known to the person skilled in the art.

A dilution phase in water or in any other mixture of solvents containing water is carried out in order to obtain a peptidic hydrolyzate characterized by a dry weight of 2 to 5 g/Kg, a concentration in peptidic nature compounds of 1 to 5 g/l, and preferentially of 1.5 to 3.0 g/l and a concentration in sugars of 0.05 to 1 g/l and preferentially of 0.1 to 0.3 g/l. The solvents used are physiologically acceptable and conventionally used by the person skilled in the art chosen from among glycerol, ethanol, propylene glycol, butylene glycol, dipropylene glycol, ethoxylated diethylene glycol or propoxylated diethylene glycol, cyclic polyols or any mixture of these solvents.

Therefore, the active agent according to the invention is advantageously solubilized in one or more physiologically suitable solvents, such as water, glycerol, ethanol, propylene glycol, butylene glycol, dipropylene glycol, ethoxylated diethylene glycol or propoxylated diethylene glycol, cyclic polyols or any mixture of these solvents. The diluted active agent is then sterilized by ultrafiltration.

After this dilution step, the peptide may be encapsulated or included in a cosmetic or pharmaceutical carrier such as liposomes or any other microcapsule utilized in the cosmetic field or adsorbed on powdery organic polymers, mineral supports such as talcs and bentonites.

According to an advantageous mode of embodiment, the active agent is present in the compositions of the invention at a concentration of between approximately 0.001% and 5%, and preferentially at a concentration of between approximately 0.01% and 1% with relation to the total weight of the final composition.

The usable compositions according to the invention may be present in the form of an aqueous solution, hydroalcoholic or oily solution; an oil in water emulsion, water in oil emulsion or multiple emulsions; they may also be present in the form of creams, suspensions or else powders. These compositions may be more or less fluid and have the appearance of a cream, lotion, milk, serum, pomade, gel, paste or foam. They may also be present in solid form, such as a stick, or may be applied on the area to be treated in aerosol form. They may be utilized as a care product and/or as a skin makeup product.

In addition, all of these compositions comprise any additive commonly utilized in the contemplated field of application as well as the adjuvants necessary for their formulation, such as co-solvents (ethanol, glycerol, benzyl alcohol, humectants, etc.), thickeners, diluents, emulsifiers, antioxidants, colorants, sunscreens, pigments, fillers, preservatives, fragrances, odor absorbers, essential oils, trace elements, essential fatty acids, surface active agents, film-forming polymers, chemical or mineral filters, moisturizing agents or thermal waters, etc. For example, one may cite hydrosoluble polymers of the natural polymer type, such as polysaccharides or polypeptides, cellulosic derivatives of the methylcellulose type or hydroxypropylcellulose type, or else synthetic polymers, poloxamers, carbomers, PVA or PVP and particularly the polymers sold by the ISP company.

In all cases, the person skilled in the art will make sure that these adjuvants as well as their proportions are chosen so as to not harm the desired advantageous properties of the composition according to the invention. These adjuvants may, for example, correspond to a concentration ranging from 0.01 to 20% of the total weight of the composition. When the composition of the invention is an emulsion, the fatty phase may represent from 5 to 80% by weight and preferably from 5 to 50% by weight with relation to the total weight of the composition. The emulsifiers and co-emulsifiers utilized in the composition will be chosen from among those conventionally utilized in the field under consideration. For example, they may be utilized in a proportion going from 0.3 to 30% by weight with relation to the total weight of the composition.

The usable compositions according to the invention may in particular consist of a shampoo, conditioner, pre- or post-aggressive hair treatment treating lotion, hairdressing cream or gel, restructuring lotion for the hair, a mask, etc. The composition may also be present in mascara form for application onto the eyelashes, eyebrows or hair.

In addition, the active agent according to the invention may be utilized alone or in combination with other active agents.

Advantageously, the usable compositions according to the invention also contain at least one other protective active agent or an agent that improves hair growth and/or health. In a non-limiting manner, the following ingredients may be cited: vitamins, anti-free radical agents, anti-UV radiation agents, other plant peptidic extracts, minoxidil, nicotinic acid esters, anti-inflammatory agents, retinoic acid or its derivatives, retinol, 5α-reductase inhibitors or peptidic compounds from chemical synthesis.

The usable composition according to the invention will be applied by any appropriate route, notably oral, parenteral or topical, and their formulations will be adapted by the person skilled in the art, in particular for cosmetic or dermatological compositions.

Advantageously, the compositions according to the invention are intended for topical administration. These compositions therefore must contain a physiologically acceptable medium, i.e., a medium compatible with the skin and epithelial appendages, and must cover all cosmetic or dermatological forms.

"Topical application" is understood to refer to the act of applying or spreading the active agent according to the invention, or a composition containing the agent, to or on the surface of the skin or a mucous membrane. "Physiologically acceptable" is understood to mean that the peptidic hydrolyzate according to the invention, or a composition containing it, is appropriate for entering in contact with the skin or mucous membrane without causing toxicity or intolerance reactions.

According to another aspect of the invention, the composition comprising the corn (*Zea mays* L.) peptidic hydrolyzate as an active agent is used to combat alopecia.

Alopecia encompasses a set of hair follicle disorders with the transient or definitive, partial or general, loss of hair as the final consequence. Men as well as women may suffer from alopecia, but the areas that are preferentially affected in men are the temporal or frontal gulfs, while diffuse alopecia of the crown is observed in women.

The second object of the invention is the use of a corn (*Zea mays* L.) peptidic hydrolyzate as an active agent capable of stimulating the hair follicle.

In fact, the inventors demonstrated that the corn (*Zea mays* L.) peptidic hydrolyzate would enable the hair follicle to be stimulated, which results in, at the molecular level, an increase in the expression of molecules from the extracellular matrix, such as fibronectin, proteins from the basal lamina, such as laminin-5. The action of the corn (*Zea mays* L.) peptidic hydrolyzate Also results in the increase in the expression of membrane proteins involved in interactions between keratinocytes (cell-cell interactions) and between keratinocytes and the extracellular matrix (cell-matrix interactions), such as beta 1 integrin. Stimulation of the hair follicle also results in the increase of expression of intracellular markers of the anagen phase, such as Ki67, p63 proliferation markers and phosphorylated histone H3, or on the contrary, in the inhibition of the expression of catagen phase initiators, such as the p53 protein, thus enabling an extension of the anagen phase of hair growth.

At the organic level, stimulation of the hair follicle manifests in the elongation of the hair in an ex vivo culture system.

The third object of the invention relates to a cosmetic treatment method intended to prevent or combat the manifestations of aging and photoaging of the hair, characterized in that the composition according to the invention is applied topically to the area to be treated.

The fourth object of the invention is the use of a corn (*Zea mays* L.) peptidic hydrolyzate as an active agent capable of stimulating the hair follicle for producing a dermato-pharmaceutical composition intended to stimulate and/or restore hair growth and limit hair loss, in the context of a preventive or curative treatment for hair loss connected to a pathological condition. From among the pathological conditions that are frequently responsible for hair loss, alopecia areata, the side effects of drug treatments and certain infections or inflammations of the scalp (psoriasis, seborrheic dermatitis, etc.) may be cited.

According to this form of the invention, the compositions will be suitable for oral administration for pharmaceutical use. Thus, the compositions may in particular be present in the form of tablets, capsules, gel capsules, chewable pastes, powders to consume as is or to be mixed immediately before use with a liquid, syrup, gels or any other form known to the person skilled in the art. These compositions also comprise any additive commonly utilized in the contemplated field of application as well as the adjuvants necessary for their formulation, such as solvents, thickeners, diluents, antioxidants, preservatives, other pharmaceutical active agents, essential oils, vitamins, essential fatty acids, etc.

Still another object of the invention is a cosmetic treatment method intended to stimulate the growth of nails, characterized in that the composition according to the invention is applied topically to the area to be treated.

Still another object of the invention is a cosmetic treatment method intended to stimulate the growth of eyelashes, or combat eyelash loss, characterized in that the composition according to the invention is applied topically to the area to be treated.

Particular embodiments of this cosmetic treatment method also result from the previous description. Other advantages and characteristics of the invention will more clearly appear upon reading the examples given for illustrative and non-limiting purposes.

BRIEF DESCRIPTION OF THE DRAWINGS

FIG. 1: A quantitative measurement of hair elongation following treatment by the hydrolyzate according to example 1 at 3%.

EXAMPLE 1

Preparation of a Peptidic Hydrolyzate From Corn Germ Cake (Zea mays L.)

The corn germ cake (Zea mays L.) is put in solution in 10 volumes of water in the presence of 2% POLYCLAR® 10 (polyvinylpyrrolidone—PVPP-insoluble). The mixture is adjusted to a pH of between 7.5 and 9.5 with an aqueous solution of sodium hydroxide 1 M.

After adjusting the pH, a mixture of bromelain at 2% and Alcalase® (Novozyme) is added in the reaction medium. The hydrolysis is obtained after 2 hours of agitation at 50° C. The enzymes are then inactivated by heating the solution to 80° C. for 2 hours. After centrifugation, the supernatant aqueous solution corresponding to a crude corn hydrolyzate is recovered.

The crude hydrolyzate purification process starts by successive filtrations by using Seitz-Orion filter plates of decreasing porosity (up to 0.2 μm) in order to obtain a bright and clear yellow solution, described as hydrolyzate 1.

At this step, the corn hydrolyzate 1 is characterized by a dry extract titrating from 20 to 30 g/kg, a protein level from 20 to 25 g/l and a sugar level from 2 to 5 g/l.

The protein nature of hydrolyzate 1 is demonstrated after electrophoresis analysis on NuPAGE® Bis-Tris Pre-cast (In-vitrogen) polyacrylamide gel. The corn protein hydrolyzate is heated to 70° C. for 10 minutes under reducing denaturing conditions (NuPAGE® LDS sample preparation buffer). A NuPAGE® Antioxidant solution is added into the inner tank (cathode) to prevent the reduced proteins from reoxidizing during the electrophoresis. Protein migration is carried out in the NuPAGE® MES migration buffer with the standard See-Blue Plus2 as a molecular weight marker. Protein coloration is carried out by using Coomassie Blue® R-250. Under these conditions, it is observed that 100% of the peptidic nature compounds have a molecular weight of less than 10 kDa.

The hydrolyzate 1 is then purified by eliminating the high molecular weight proteins by ultrafiltration using the Pellicon® 2 Biomax 5 kDa cassette. After this step, 90% of peptidic nature compounds from the hydrolyzate have a molecular weight of less than 5 kDa.

After this final purification, a hydrolyzate having a dry weight of 9.7 g/Kg is obtained; 6.2 g/l of peptidic nature compounds and 0.6 g/l of sugars. A dilution phase is then carried out in a water-glycerol mixture to obtain a peptidic hydrolyzate characterized by a dry weight of 2 to 5 g/Kg, a concentration in peptidic nature compounds of 1.5 to 3.0 g/l and a concentration in sugars of 0.1 to 0.3 g/l. This peptidic hydrolyzate corresponds to the active agent according to the invention.

This peptidic hydrolyzate is then analyzed by high pressure liquid chromatography (HPLC) by using an HP1100 apparatus run by the ChemStation software. The column used during elution of hydrolyzate 2 is a Nucleosil® 300-5 C4 MPN (125×4 mn), enabling the proteins having molecular weights from 0.2 to 25 kDa to be chromatographed (according to a suitable solvent gradient). Under these chromatographic conditions, several peptidic fractions could be identified.

The determination of the composition in amino acids of the active agent according to the invention was also carried out. After the proteins and peptides are measured by the Lowry method, an acid hydrolysis is produced to reduce all the peptides in the free amino acid state. An example of the amino acid composition of the hydrolyzate is given in the following table. The values are expressed as a percentage of amino acids for 100 g of proteins.

| Amino acids | % |
|---|---|
| Alanine | 9.4 |
| Aspartic Acid | 7.2 |
| Arginine | 3.6 |
| Glutamic Acid | 23.7 |
| Glycine | 3.6 |
| Histidine | 2.2 |
| Isoleucine | 4.5 |
| Leucine | 16.1 |
| Lysine | 2.2 |
| Phenylalanine | 6.7 |
| Proline | 10.3 |
| Serine | 6.3 |
| Threonine | 4.0 |
| Tyrosine | 5.8 |
| valine | 5.4 |
| Tryptophan | <0.5 |

EXAMPLE 2

Demonstration of the Stimulation of Hair Growth by the Hydrolyzate According to Example 1

The goal of this study is to determine the influence of the hydrolyzate according to example 1 on human hair growth. To do this, the elongation of the hair shaft extending the hair follicles cultivated ex vivo is measured.

Protocol:

6-mm diameter skin punch biopsies from facelifts containing hair follicles are cultured on inserts in a WILLIAM E medium. On day 0, the biopsies are shaved, and then every 24 hours the skin explants are treated with 20 μl of a solution at 3% of the hydrolyzate according to example 1, deposited on the biopsy for 14 and 17 days. Untreated controls are carried out in parallel.

Photos are taken by using the CCD Vivacam camera from Vivascope 1500® (Europe Mavig) and the hair length of each follicle is evaluated by using the "Image Pro Analyser 6.3" software.

Results:

The hair length is expressed in μm (see FIG. 1). In the presence of 3% hydrolyzate according to example 1, hair elongation is multiplied by 3.37 after 14 days and by 2.26 times after 17 days.

Conclusion:

The hydrolyzate according to example 1 very significantly stimulates hair growth.

EXAMPLE 3

Demonstration of the Stimulation of Hair Follicle Cellular Activity by the Hydrolyzate According to Example 1

The object of this study is to show the stimulating effect on cellular functions, and in particular, on hair follicle cell renewal of the hydrolyzate according to example 1. To do this, the cellular proliferation markers (Ki67), epidermal renewal markers (p63) and mitosis markers (phosphorylated histone 3), as well as a marker of the entrance into catagen phase, have been studied.

Protocol:

Human skin biopsies are cultured under the same conditions as in example 2, and then treated for 48 hours by the hydrolyzate according to example 1 at 1%. Untreated controls are also carried out. At the end of the experiment, the biopsies are included in the OTC resin and frozen in nitrogen. Sections of approximately 6 μm are then made by the cryostat. The sections are collected on polylysinated observation slides and then the sections are fixed in an acetone bath (previously maintained at −20° C.) for 10 minutes. Immunolabeling is carried out by using an anti-Ki67 polyclonal antibody (Abcam) or an anti-phosphorylated histone 3 polyclonal antibody (Abcam) or an anti-p63 monoclonal antibody (Tebu, SantaCruz) or an anti-p53 monoclonal antibody (Dako). A suitable secondary antibody, paired with a fluorescent marker is then put in contact with the sections. The follicle sections are then examined by epifluorescence microscope (Nikon Eclipse E 80i microscope).

Results:

On the follicle sections of hair treated by the hydrolyzate according to example 1, it is observed that a higher number of cells from the outer root sheath are labeled for Ki67, phosphorylated histone 3 and p63. On the contrary, the cells labeled by the p53 antibody are fewer in comparison with the untreated control.

An increase of 18.5% for Ki67, 7.1% for phosphorylated histone 3 and 19.1% for p63 may be measured by using fluorescence quantification software.

Conclusions:

The hydrolyzate according to example 1 increases the expression of cellular activity proliferation markers, thus demonstrating stimulation of follicle activity. On the other hand, the hydrolyzate according to example 1 reduces the expression of p53 involved in the induction of the catagen phase.

EXAMPLE 4

Demonstration of the Activating Effect of the Hydrolyzate According to Example 1 on the Extracellular Matrix, on the Cell-Matrix Connections and on the Cell-Cell Connections in the Hair Follicle The object of this study is to determine the influence of the hydrolyzate according to example 1 on the expression of molecules from the extracellular matrix (fibronectin), proteins from the basal lamina (laminin-5) and proteins involved in cell-cell interactions and cell-matrix interactions (beta 1 integrin).

Culture Protocol:

Human skin biopsies are cultured under the same conditions as in example 2, and then treated for 48 hours by the hydrolyzate according to example 1 at 1%. Untreated controls are also carried out.

Beta 1 Integrin Immunolabeling Protocol:

At the end of the experiment, the biopsies are placed on a cassette and immersed in a mixture of formol at 10% for 2 hours in an automated apparatus (VIP). The paraffin coating is prepared by a series of alcohol baths (at increasing concentration and time), followed by 2 xylene baths and lastly a paraffin bath. The total duration of this series of operations is a dozen hours. The biopsies included in paraffin are then cut at 4 μm by a microtome and mounted on slides. The paraffin is removed from the slides, the slides are rehydrated and then subjected to immunolabeling by a monoclonal antibody directed against beta 1 integrin (Tebu, Santa Cruz), and then by a suitable secondary antibody paired with a fluorescent marker. The skin sections are then examined by epifluorescence microscope (Nikon Eclipse E 80i microscope).

Laminin-5 (or Laminin 332 According to the New Nomenclature) Immunolabeling Protocol:

At the end of the experiment, the biopsies are included in paraffin as with for beta 1 integrin immunolabeling. The paraffin is removed from the slides, the slides are rehydrated and then subjected to an unmasking step prior to immunolabeling by a monoclonal antibody directed against laminin 332 (Chemicon). A suitable secondary antibody, paired with a fluorescent marker is then put in contact with the sections. The skin sections are finally examined by epifluorescence microscope (Nikon Eclipse E 80i microscope).

Fibronectin Immunolabeling Protocol:

At the end of the experiment, the biopsies are included in the OTC resin and frozen in nitrogen. Sections of approximately 6 μm are then made by the cryostat. The sections are collected on polylysinated observation slides and then the sections are fixed in an acetone bath (previously maintained at −20° C.) for 10 minutes. Immunolabeling is carried out by using a specific rabbit polyclonal antibody (Sigma). A suitable secondary antibody, paired with a fluorescent marker is then put in contact with the sections. The skin sections are finally examined by epifluorescence microscope (Nikon Eclipse E 80i microscope).

Results:

On the sections of hair follicle treated by the hydrolyzate according to example 1, in which the laminin-5 was immunolabeled, a more intense fluorescence of the basal lamina (area in which the laminin-5 is located) is observed.

On the sections of hair follicle treated by the hydrolyzate according to example 1, in which the fibronectin was immunolabeled, a more intense fluorescence of the extracellular matrix (area in which the fibronectin is located) is observed.

On the sections of hair follicle treated by the hydrolyzate according to example 1, in which the beta 1 integrin was immunolabeled, a more intense fluorescence of the periphery of epithelial cells of the outer sheath was observed. An increase on the order of 244% of beta 1 integrin may be measured by using fluorescence quantification software.

Conclusions:

The hydrolyzate according to example 1 improves the quality of the extracellular matrix, cell-cell adhesion and cell-matrix adhesion.

EXAMPLE 5

Preparation of Compositions

1—Anti-Hair Loss Treating Milk:

The product is designed to be vaporized onto the scalp and onto damp hair. Massage to distribute the product uniformly. Combats hair loss while making the hair smooth and easy to style.

| | | Formulation | | |
|---|---|---|---|---|
| | | 1 Weight | 2 Weight | |
| INCI name | Trade name | percent | percent | Supplier |
| Deionized Water | — | qsp | qsp | |
| Polyquaternium-11 | Gafquat ® 755N | 1.25 | 2.00 | ISP |
| Propylene Glycol (and) Diazolidinyl Urea (and) Iodopropynyl Butylcarbamate/ | Liquid Germall ® Plus | 0.50 | 0.50 | ISP |
| Sodium Polyacrylate (and) Hydrogenated Polydecene (and) Trideceth-6/ | RapiThix ™ A-60 | 0.50 | 0.50 | ISP |
| | Hydrolyzate according to example 1 | 0.1 | 0.5 | ISP |
| | Total | 100.00 | 100.00 | |

Place water in a suitable container and start agitation. Add the Gafquat 755N and the Liquid Germall Plus and agitate until a uniform appearance is obtained. Add the RapiThix A-60 and agitate until a uniform appearance is obtained (approximately 15 minutes). Add the hydrolyzate according to example 1 and agitate until a uniform appearance is obtained. Dispose the product in a non-aerosol vaporizer equipped with a Calmar Mark VI WL31 pump.

2—Serum for Hair Growth

Apply the product to the damp scalp. Massage to distribute the product uniformly. Promotes hair growth or regrowth while making the hair more vigorous.

Disperse the Natrosol 250HHR and the Disodium EDTA in water under agitation. Heat to 50-60° C., and agitate until a uniform appearance is obtained. Add the Styleze® CC-10 and agitate until a uniform appearance is obtained. Allow to cool to ambient temperature and add the ingredients in the order listed by agitating until a uniform appearance between them is obtained.

3—Anti-Age Care for Hair and Scalp

Apply the product to the damp scalp. Massage to distribute the product uniformly. Combats hair aging and weakening while making the hair smooth and easy to style.

| | | Formulation | | |
|---|---|---|---|---|
| | | 1 Weight | 2 Weight | |
| INCI name | Trade name | percent | percent | Supplier |
| Water | | qsp | Qsp | |
| Hydroxyethylcellulose | Natrosol 250HHR | 0.35 | 0.50 | Hercules/Aqualon |
| Disodium EDTA | Dissolvine NA-2S | 0.05 | 0.05 | Akzo Nobel |
| VP/DMAPA Acrylates Copolymer | Styleze ® CC-10 | 5.00 | 5.00 | ISP |
| Quaternium-26 | Ceraphyl ® 65 | 1.00 | 1.00 | ISP |
| Panthenol | Ritapan DL | 0.15 | 0.15 | RITA |
| Propylene Glycol (and) Diazolidinyl Urea (and) Iodopropynyl Butylcarbamate | Liquid Germall ® Plus | 0.50 | 0.50 | ISP |
| | Hydrolyzate according to example 1 | 1.00 | 1.00 | ISP |
| Total | | 100.00 | 100.00 | |

| INCI name | Trade name | Formulation 1 Weight percent | Formulation 2 Weight percent | Supplier |
|---|---|---|---|---|
| Phase A | | | | |
| Deionized Water | — | qsp | qsp | |
| Aminomethyl Propanol | AMP-95 | 0.05 | 0.05 | |
| Acrylic Acid/VP Crosspolymer | UltraThix ™ P-100 | 0.85 | 0.85 | ISP |
| Phase B | | | | |
| Gycerol Dilaurate | Emulsynt ™ GDL | 0.50 | 0.50 | ISP |
| Jojoba Seed Oil | — | 2.00 | 2.00 | Lipo |
| Cetearyl Alcohol | — | 2.00 | 2.00 | Rita |
| Phase C | | | | |
| Cyclopentasiloxane | SiTec ™ CM040 | 0.50 | 1.00 | ISP |
| Phase D | | | | |
| VP/DMAPA Acrylates Copolymer | Styleze ® CC-10 | 3.00 | 3.00 | ISP |
| Water | | 20.00 | 20.00 | |
| Aminomethyl Propanol | | 0.37 | 0.37 | |
| Phase E | | | | |
| Diazolidinyl Urea (and) Methylparaben (and) Propylene Glycol | Germaben ® M | 0.75 | 0.75 | ISP |
| | Hydrolyzate according to example 1 | 0.50 | 1.00 | ISP |
| Total | | 100.00 | 100.00 | |

Place water and AMP-95 in a container under agitation. Add the UltraThix™ P-100 to the water under vigorous agitation and maintain under agitation for 30 minutes. Heat phase A to 65° C. Heat the ingredients of phase B to 65° C. and then blend them. Add to phase B and mix carefully. Cool to 35° C. Add phase C to the main mixture and mix until a uniform appearance is obtained.

Independently, mix the ingredients of phase D until a uniform appearance is obtained. Add the Germaben® M (Phase E) and mix until a uniform appearance is obtained. Add the hydrolyzate according to example 1 and agitate until a uniform appearance is obtained.

What is claimed is:

1. A method of cosmetic treatment, the method comprising:
   providing a cosmetic composition comprising at least one *Zea mays* L. peptidic hydrolysate comprising 90% of peptidic nature compounds having a molecular weight of less than 5 kDa, as an active agent to stimulate hair growth or reduce hair loss; and
   applying the cosmetic composition topically to an area having hair follicles.

2. The method of claim 1, wherein the peptidic hydrolyzate is solubilized in one or more physiologically acceptable solvents, selected from the group consisting of water, glycerol, ethanol, propylene glycol, butylene glycol, dipropylene glycol, ethoxylated diethylene glycol or propoxylated diethylene glycol, cyclic polyols, or any mixture of these solvents.

3. The method of claim 1, wherein the peptidic hydrolyzate contains between 1 and 5 g/l of peptidic nature compounds.

4. The method of claim 3, wherein the peptidic hydrolyzate contains between 1.5 and 3.0 g/l of peptidic nature compounds.

5. The method of claim 1, wherein the peptidic hydrolyzate is used in a quantity representing from 0.001% to 5% of the total weight of the composition.

6. The method of claim 5, wherein the peptidic hydrolyzate is used in a quantity representing from 0.01% to 1% of the total weight of the composition.

7. The method of claim 1, wherein the composition further comprises one other active agent protecting or improving hair growth selected from the group consisting of vitamins, other plant peptidic extracts, minoxidil, nicotinic acid esters, retinoic acid, retinol.

8. The method of claim 1, wherein the cosmetic composition combats alopecia.

9. The method of claim 1, wherein the peptidic hydrolyzate stimulates the hair follicle.

10. The method of claim 9, wherein the peptidic hydrolyzate increases the expression of at least one of laminin-5, beta integrin 1, and fibronectin.

11. The method of claim 9, wherein the peptidic hydrolyzate increases the expression of protein p63, marker Ki67 and the phosphorylation of histone 3 in cells of the outer root sheath of the hair follicle.

12. The method of claim 9, wherein the peptidic hydrolyzate increases hair elongation.

13. The method of claim 1, wherein the area having hair follicles is the eyelid to treat the eyelashes.

14. The method of claim 1, wherein the cosmetic composition is a dermato-pharmaceutical composition, and the area having hair follicles is affected by a pathological condition effecting hair growth or hair loss thereof.

15. The method of claim 14, wherein the pathological condition is alopecia areata, hair loss resulting from a drug treatment, an infection or inflammation of the scalp that causes hair loss.

* * * * *

UNITED STATES PATENT AND TRADEMARK OFFICE
CERTIFICATE OF CORRECTION

PATENT NO. : 9,259,381 B2  
APPLICATION NO. : 13/858262  
DATED : February 16, 2016  
INVENTOR(S) : Claude Dal Farra et al.

Page 1 of 1

It is certified that error appears in the above-identified patent and that said Letters Patent is hereby corrected as shown below:

On the Title Page, Item (54) and in the Specification, Column 1

The Title reads "USE OF A CORN PEPTIDIC HYDROLYZATE AS AN ACTIVE AGENT STIIMULATING HAIR GROWTH"

It should read:

-- USE OF A CORN PEPTIDIC HYDROLYZATE AS AN ACTIVE AGENT STIMULATING HAIR GROWTH --

Signed and Sealed this  
Third Day of May, 2016

Michelle K. Lee  
*Director of the United States Patent and Trademark Office*